United States Patent [19]

Richards et al.

[11] Patent Number: 5,207,635
[45] Date of Patent: May 4, 1993

[54] ORTHOPEDIC DEVICE FOR PROVIDING LOWER BACK SUPPORT

[76] Inventors: Ronald G. Richards; Joseph J. Dillon, both of 175 Wicks La., Malverne, N.Y. 11565

[21] Appl. No.: 842,797

[22] Filed: Feb. 27, 1992

Related U.S. Application Data

[63] Continuation of Ser. No. 594,123, Oct. 9, 1990, abandoned, which is a continuation of Ser. No. 396,365, Aug. 21, 1989, abandoned.

[51] Int. Cl.⁵ .................. A61F 5/37; A61F 5/30
[52] U.S. Cl. ..................... 602/19; 482/124; 2/44; 128/876
[58] Field of Search ............ 128/78, 68, 69, 870, 128/876; 2/44; 272/119, 143; 606/237; 482/124, 131; 602/13, 19

[56] References Cited

U.S. PATENT DOCUMENTS

| | | | |
|---|---|---|---|
| 3,441,027 | 4/1969 | Lehman | 602/19 X |
| 3,717,143 | 2/1973 | Johnson | 128/78 |
| 4,245,628 | 1/1981 | Eichler | 128/78 |
| 4,475,543 | 10/1984 | Brooks et al. | 128/78 |
| 4,597,386 | 7/1986 | Goldstein | 128/78 |
| 4,627,109 | 12/1986 | Carabelli et al. | 2/44 |
| 4,682,588 | 7/1987 | Curlee | 128/78 |
| 4,789,372 | 12/1988 | Wicks | 2/44 X |
| 4,833,730 | 5/1989 | Nelson | 2/44 |
| 4,836,194 | 6/1989 | Sebastian et al. | 128/78 |
| 4,884,295 | 12/1989 | Cox | 2/44 X |
| 4,905,993 | 3/1990 | Barone | 602/19 X |
| 4,907,576 | 3/1990 | Curlee | 128/78 |
| 4,955,608 | 9/1990 | Dougherty et al. | 272/119 X |
| 5,120,288 | 6/1992 | Sinaki | 482/105 |

FOREIGN PATENT DOCUMENTS

| | | | |
|---|---|---|---|
| 0238183 | 9/1987 | European Pat. Off. | 128/78 |
| 1197192 | 7/1965 | Fed. Rep. of Germany | 128/78 |

*Primary Examiner*—David Isabella
*Assistant Examiner*—D. Willse
*Attorney, Agent, or Firm*—Amster, Rothstein & Ebenstein

[57] ABSTRACT

An orthopedic device to provide lower back support for a wearer includes a flexible flat body, a resilient contoured lumbar support pad of varying thickness secured to the body, and a flexible belt traversing the pad and secured to the body at points beyond the pad, the belt being configured and dimensioned to be secured about the waist of the wearer for positioning the pad on the lumbar region of the wearer.

17 Claims, 5 Drawing Sheets

ORTHOPEDIC DEVICE FOR PROVIDING LOWER BACK SUPPORT

This is a continuation of copending application Ser. No. 07/594,123, filed on Oct. 9, 1990, now abandoned, which is a continuation-in-part of application Ser. No. 07/396,365, filed on Aug. 21, 1989, now abondoned.

BACKGROUND OF THE INVENTION

1. Field of the Invention

The invention relates generally to an improved orthopedic device for lower back support during work, exercise, and competition.

2. Description of the Prior Art

Exercise and weight training belts are used to provide lower back support to avoid injury to this area when under stress from activity. The range of use of these devices is broader than generally thought. For example, truck drivers use them on extended trips, and construction workers use them when lifting heavy loads on the job. Regardless of the reasons for use, currently there is no belt that properly addresses the most sensitive area of the back, the lumbar region —— that is, the area of the lumbar vertabrae and surrounding erector muscles down to the small of the back. Devices of the prior art are belts whose construction provides for support along its horizontal center with support diminishing as a person moves above or below this center. At the lumbar region, these devices bridge across the spine via the erector muscles, leaving a gap at the center of the back.

More particularly, conventional orthopedic devices do not afford balanced, equal, and uninterrupted support to the lumbar region along the entire horizontal and vertical planes thereof.

The first part of the problem is to supply uninterrupted support across the back along the horizontal plane. The problem arises because conventional belts are of flat, single level construction. Some belts have lumbar pads, but these pads are also flat or of one piece construction. The back, across the lumbar area, is indented and curved. The erector muscles are indented from the flat of the back, and the spine is further indented at the center of the back. Thus, belts of flat construction can not provide even, uninterrupted support in the horizontal plane.

The second part of the problem is to supply equal support or pressure uniformly from the top to the bottom of the belt along the vertical plane. Conventional belts are constructed in one of three basic ways: single unit with a single fastener, single units with dual fasteners, and two part construction —— i.e., a wide body with a narrow support belt affixed with a fastener. The single unit belts with one fastener and the two part construction belts tend to concentrate the support pressure along the horizontal center of the belt. This support decreases to almost zero at the upper and lower edges of the belt. The single unit-dual fastener construction belts have the problem of the upper and lower edges of the belt digging into the back of the wearer and the center of the belt bowing outwardly, thereby giving unequal support in the vertical plane.

Accordingly, it is an object of the present invention to provide an orthopedic device affording balanced, equal, and uninterrupted support to the lumbar region along the entire horizontal and vertical planes thereof.

Another object is to provide such a device which is of simple and rugged construction and economical to manufacture, use and maintain.

SUMMARY OF THE INVENTION

It has now been found that the above and related objects are obtained in an orthopedic device, to provide lower back support for a wearer, according to the present invention. The device comprises a flexible flat body, a resilient contoured lumbar support pad of varying thickness secured to said body, and a flexible belt traversing the pad and secured to the body at points beyond the pad, the belt being configured and dimensioned to be secured about the waist of the wearer for positioning the pad on the lumbar of the wearer.

In a preferred embodiment, the body is of one-piece, integral, unitary construction and has a pair of opposed faces, the pad being secured to the face adjacent the wearer, when worn, and the belt being secured to the opposite face. The pad comprises a plurality of articulated sections including a center section of at least a first thickness adapted to be positioned over the spine of the wearer and wide enough to bridge the gap at the spine between the erector muscles of the wearer, and at least one side section of a second thickness disposed on each side of the center section and adapted to be positioned adjacent the erector muscles of the wearer, the first thickness being substantially greater than the second thickness. The center section has a thickness along its central vertical axis which is greater than its thickness to either side. The pad extends substantially from the top of the belt to the bottom of the belt, and preferably substantially from the top of the body to the bottom of the body, thereby to provide support at the lumbar of the wearer across the width of the device.

In one preferred embodiment, the belt consists essentially of two vertically spaced straps secured to the body in parallel disposition and releasable fastener means secured thereto for securing the ends of each strap independently about the wearer's waist. The pair of straps optimally trisect the height of the body.

In another preferred embodiment, the belt consists essentially of a single strap and releasable fastener means secured thereto for securing the belt about the wearer's waist. The strap is preferably secured to the body in a generally elliptical configuration, the strap having one end secured to a first point at the center of one end of the body, extending in an upward arc, with the apex of the upward arc near the upper edge of the middle of the body, and descending to a second point at the center of the opposite end of the body, where the strap forms a loop extending beyond the opposite body end and is secured to the second point. The strap also extends from the second point in a downward arc, with the nadir of the downward arc near the lower edge of the middle of the body opposite the apex, and rises to cross-join and overlap the strap one end at the first point, thereby to complete the generally elliptical configuration. Finally the strap extends beyond the one body end to form a tongue for fastening. The fastener means is preferably a tape fastener system affixed to the outside face of the tongue and includes a fastener frame defining a slot, the loop of the strap extending through the slot.

The device of the present invention provides uninterrupted support across the back along the horizontal plane due to the multilevel and articulated configuration of the pad providing three levels of construction; in addition to the general flat level of the body of the device, there are the two additional levels of the contoured lumbar pad. This construction enables the device to fit more uniformly across the back, providing uninterrupted support. The device of the present invention provides equal support or pressure uniformly from the top to the bottom of the belt along the vertical plane due to its use of the body as a platform for mounting either a single elliptical strap system or two separate parallel straps vertically spaced so as to distribute pressure uniformly throughout the width of the belt in the lumbar region.

The present invention also encompasses an orthopedic device to provide lower back support for a wearer, comprising a resilient contoured lumbar support pad of varying thickness having a pair of opposed ends and a flexible belt traversing the pad and operatively secured thereto adjacent the opposed pad ends, the belt being configured and dimensioned to be secured about the waist of the wearer for positioning the pad on the lumbar region of the wearer.

BRIEF DESCRIPTION OF THE DRAWING

The above brief description, as well as further objects and features of the present invention, will be more fully understood by reference to the following detailed description of the presently preferred, albeit illustrative, embodiments of the present invention when taken in conjunction with the accompanying drawing wherein:

FIG. 4 is a schematic view showing the various steps in the manufacture of the lumbar support pad; and.

DESCRIPTION OF THE PREFERRED EMBODIMENTS

Figure 1A:
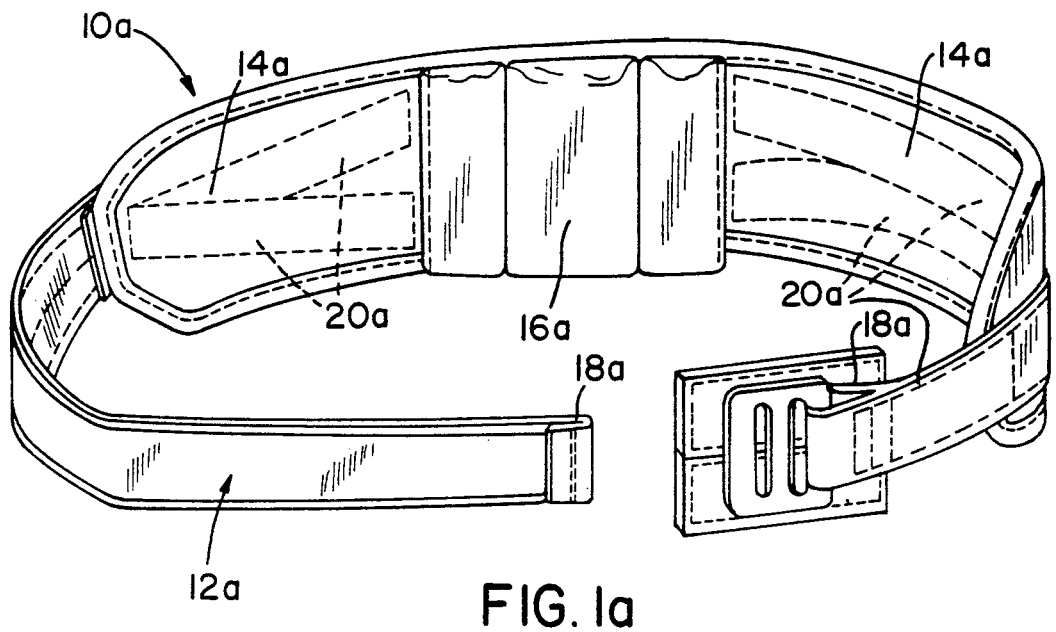
FIG. 1a is an isometric view showing an embodiment of the lumbar support pad on the single fastener belt.
Figure 1B:
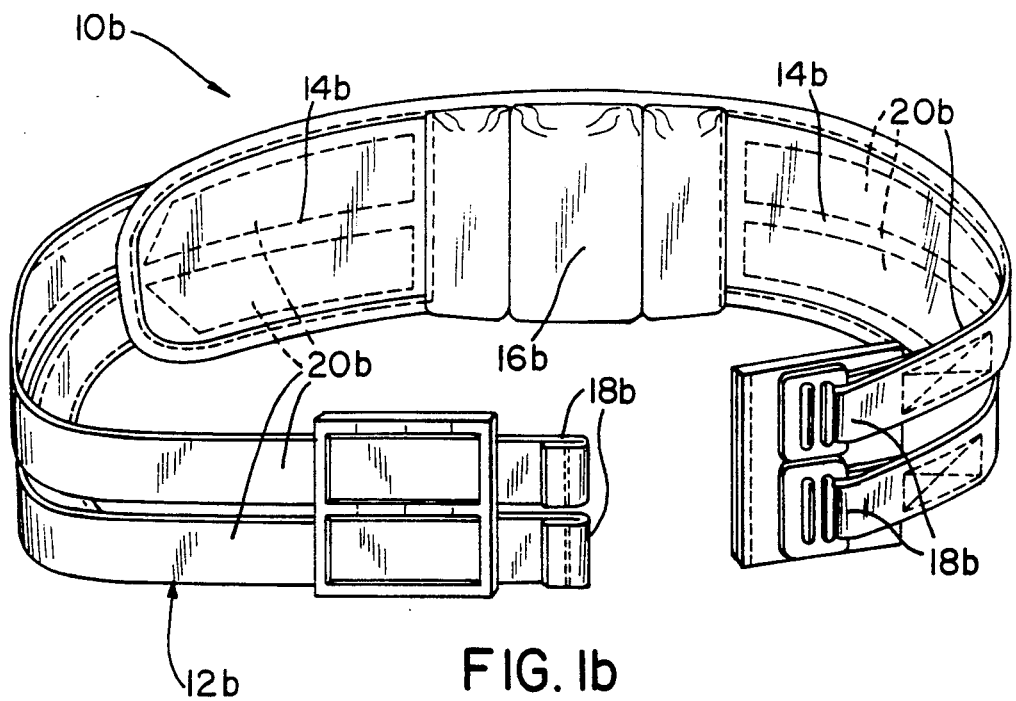
FIG. 1b is an isometric view showing an embodiment of the lumbar support pad on the dual fastener belt.

Referring now to the drawing, and in particular to FIGS 1a and 1b thereof, therein illustrated are two embodiments of an orthopedic device according to the present invention, generally designated by the reference numeral 10. Each embodiment comprises basically a flexible belt generally designated by the reference numeral 12, a flexible flat body generally designated 14 attached to the belt 12, and a resiliently contoured lumbar support pad generally designated 16 centrally attached to the body 14. Each belt 12 is in turn formed of at least one strap 20 and at least one fastener 18, the strap 20 transversing the pad 16 and being secured to the body at points laterally beyond the pad 16 for positioning the pad 16 on the wearer. More particularly, FIG. 1a illustrates a device 10a with one strap 20a adapted to be secured to the wearer with a single fastener 18a, and FIG. 1b illustrates a device 10b with two straps 20b adapted to be secured to the wearer with a dual fastener 18b.

Figure 2:
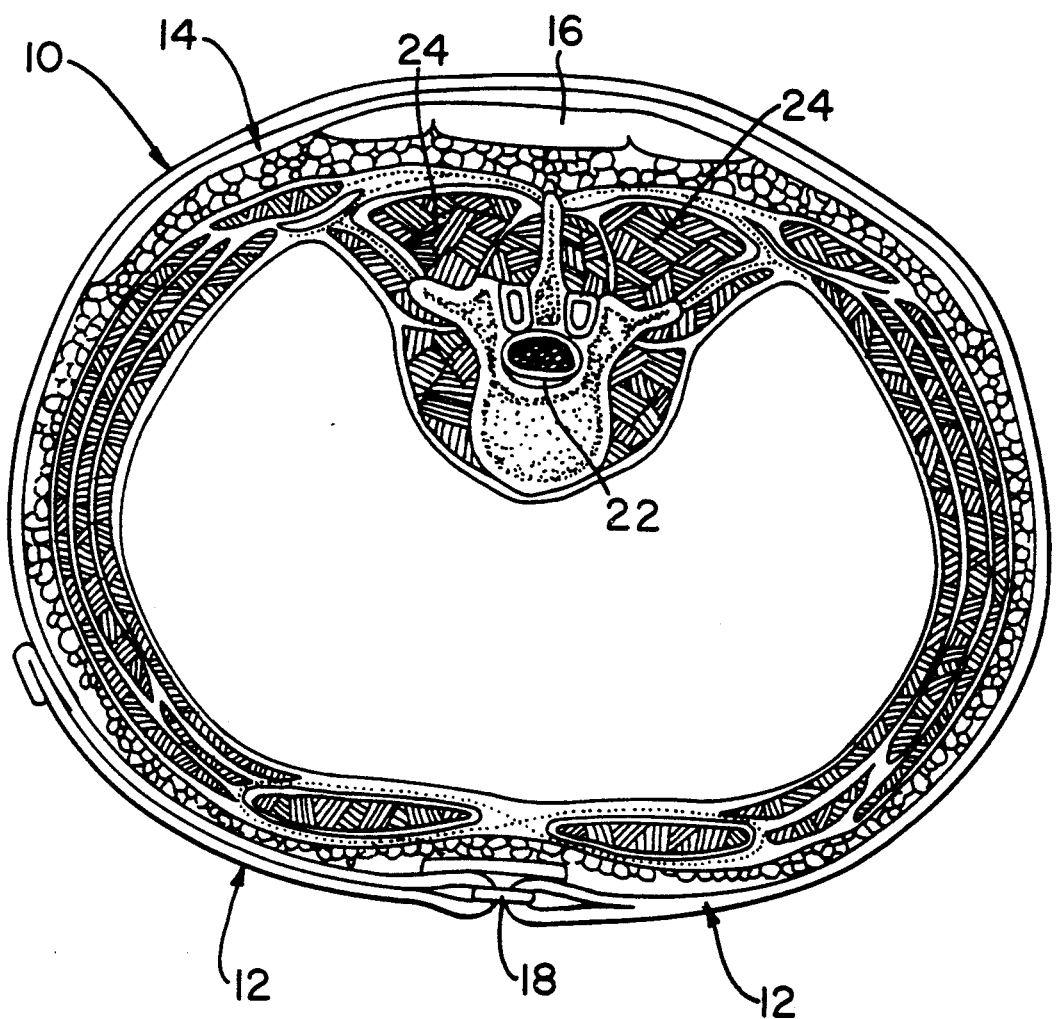
FIG. 2 is a sectional plan view of the lumbar area, with the belt worn around the user's waist, looking down.

Referring now to FIG. 2, the device 10 is shown secured to the wearer, in an overhead sectional view, looking down, with the wearer's spine at the top of the drawing. The multisection bilevel articulated contoured lumbar support pad 16 conforms to the contour of the back in the lumbar area, providing support to the vertabrae 22 and surrounding erector muscles 24.

Figure 3A:
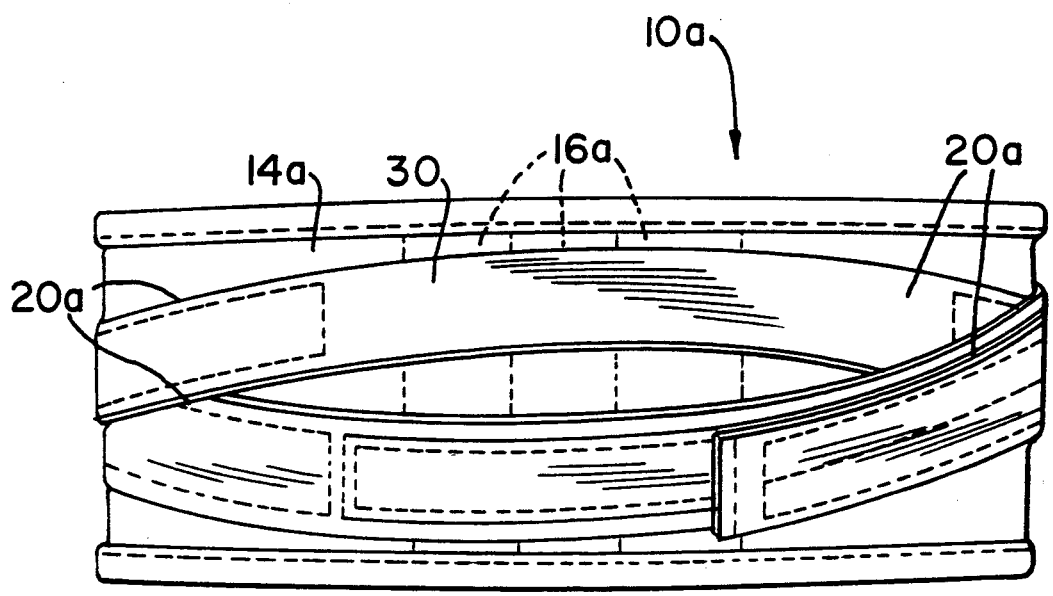
FIG. 3a is a fragmentary rear elevational view of the single elliptical strap-single fastener embodiment.
Figure 3B:
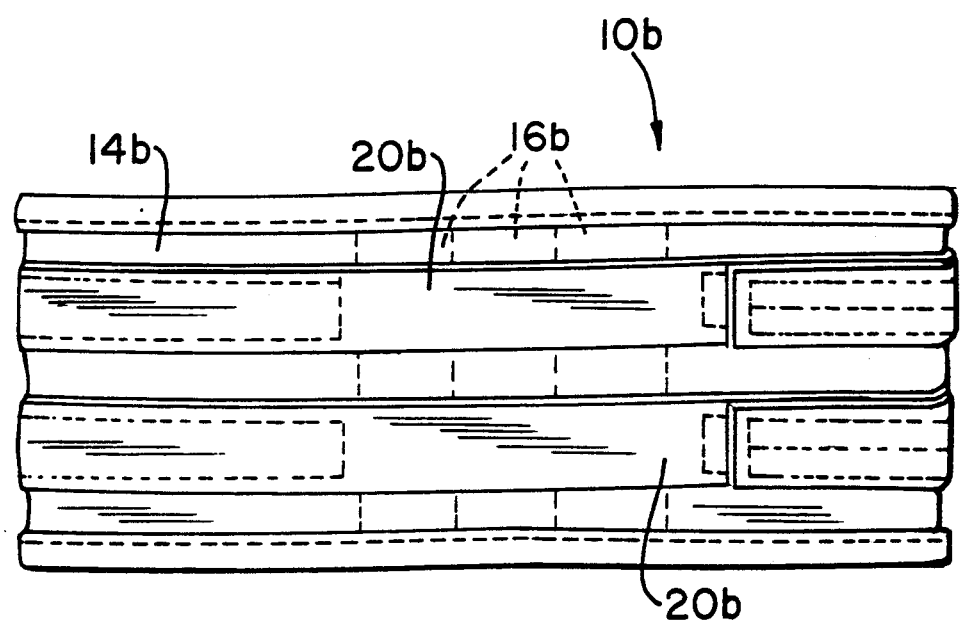
FIG. 3b is a fragmentary rear elevational view of the dual strap support-dual fastener embodiment.

Referring now to FIGS. 3A and 3B, therein illustrated are the two embodiments 10a and 10b, respectively. The strap design of each provides balanced distribution of support from the top of the device to the bottom of the device, where it covers the lumbar region of the back. Referring now to FIG. 3a, the single strap construction device 10a has a single strap 20a configured in an elliptical pattern. The strap 20a is secured to body 14a (e.g., by stitching) exclusively beyond the lumbar support pad 16a, the left side of top strap portion 30 being stitched over bottom strap portion 32, and the right side of top strap portion 30 being stitched under bottom strap portion 32. This construction pulls across the back freely and equally through the width of the device 10a. The elliptical construction gives the support of dual straps in the rear against the lumbar area, with the convenience and comfort of a single strap 20a with a single fastener 18a in front (see FIG. 1a).

Referring now to FIG. 3b, the dual strap support construction device 10b has two vertically spaced straps 20b in a parallel dual strap-dual fastener configuration with the straps 20b attached to the body 14b (e.g., by stitching) exclusively beyond the lumbar support pad 16b and in parallel disposition. This construction provides dual strap support across the rear of the device 10b, with the added ability of precise adjustment of each strap 20b for maximum precision of fit (see FIG. 1b). The two straps 20b optimally trisect the body 14b into three sections of generally equal width along a vertical axis.

Figure 4:
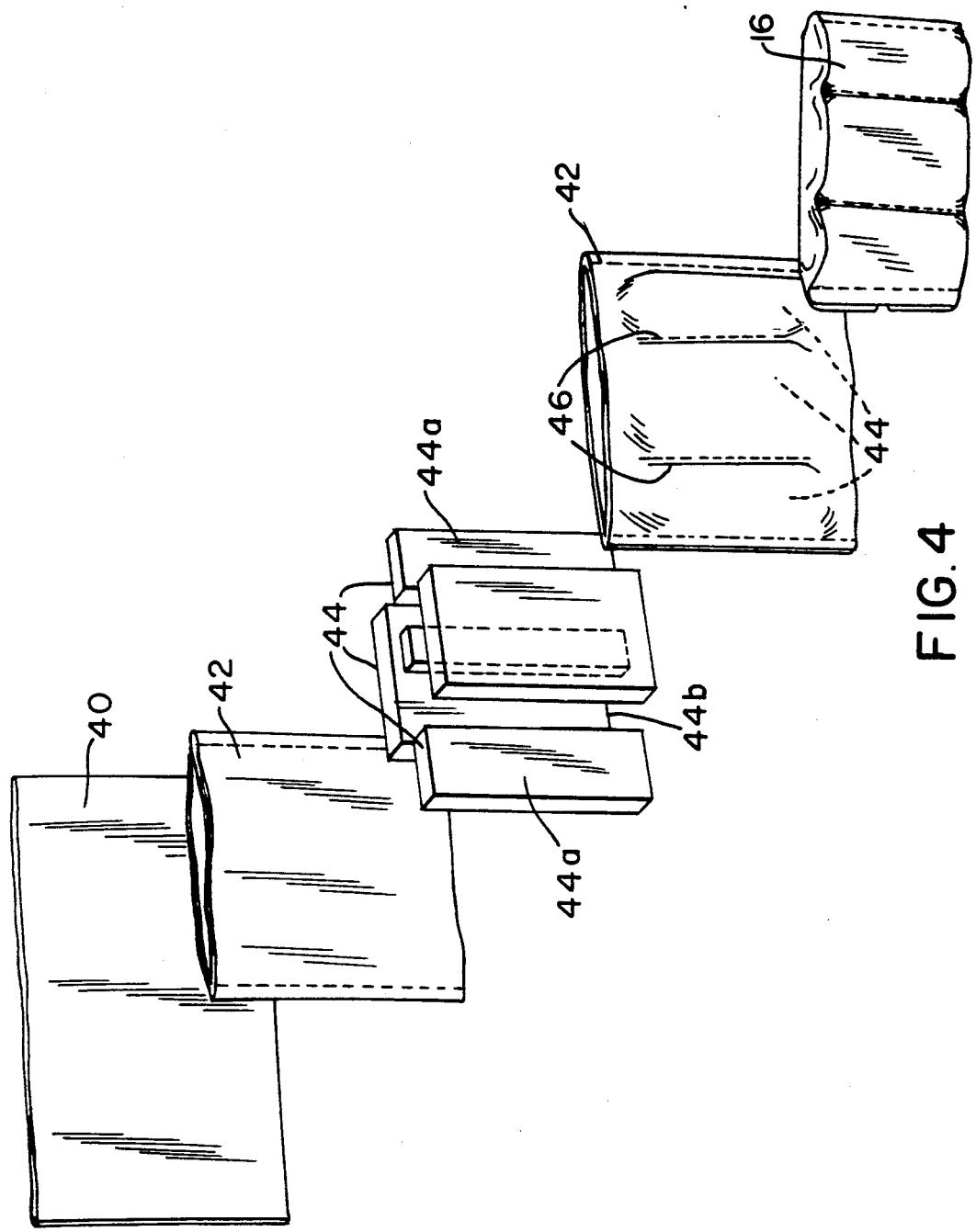

FIG. 4 is a schematic view showing the stages of a preferred method of construction of the lumbar support pad 16. Beginning with a rectangular sheet of synthetic fiber web pack cloth 40, the cloth is fashioned into an envelope 42 to accommodate the precut synthetic rubber sections 44 that form the pad. There are three lateral or side-by-side sections: two single piece outer sections 44a of equal size that are to be positioned at the erector muscles, and a larger and thicker three piece center section 44b that forms a camber or inwardly convex shape to fill the gap between the erector muscles 24 and the spine 22, as best seen in FIG. 2. An overhead sectional view of the center section 44b, with the base at the bottom of the view, resembles the cross section of a railroad rail or an I-beam, optionally with rounded edges. The sections of synthetic rubber 44a, 44b are inserted into the envelope 42, and the envelope 42 is stitched at 46, between each individual section, to form the articulated multisection contoured lumbar support pad 16. The remaining cloth of the envelope 42 above and below the padding 44a, 44b is optionally folded behind the padding and stitched in this position to provide the finished lumbar support pad 16. Clearly the lumbar support pad 16 can be formed in other ways as well —— e.g., using a single precut or molded synthetic rubber section of appropriate configuration within the envelope for either the center section 44b or even the entire padding 44.

Figure 5:
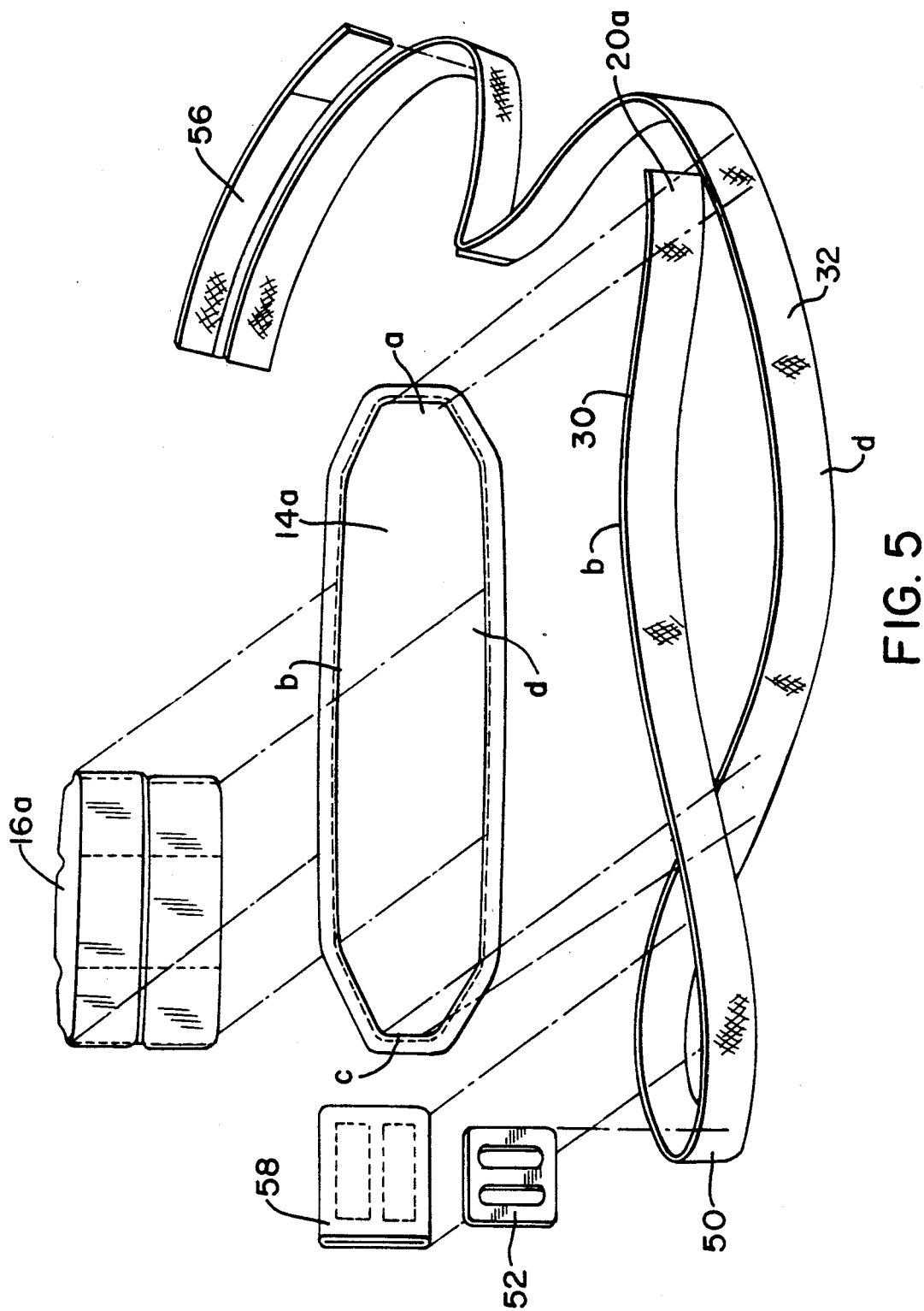
FIG. 5 is an exploded isometric view from the back of the single elliptical strap belt-single fastener embodiment.

FIG. 5 is an exploded view from the back showing preferred construction of the single strap-single fastener embodiment 10a and its elliptical cross-joining strap configuration. Strap 20a is anchored on the outer face of body 14a at one center end point a. The strap is disposed in an upward arc reaching its apex b near the upper edge of the middle of the body 14a and then descending to complete the arc at the opposite center end point c of the body 14a, where it turns inward to form a loop 50 extending through a slot of fastener frame 52 and returns to end point c. The strap 20a then descends from end point c of the body 14a in a downward arc reaching its nadir d near the lower edge of the middle of the body 14a (opposite the apex b) and then rises to cross-join and overlap the point of origin a, completing the elliptical circuit abcd. Finally, the strap 20a extends beyond point a to form a tongue or free end 54 for fastening.

The multisection bilevel articulated contoured lumbar support pad 16a is now secured centrally to the inner face of body 14a, for example, by stitching. Tape fastener system 56 may be secured to the outer face of tongue 54 either before or after application of strap 20a to the body 14a. A pad 58 is preferably applied to strap 20a behind fastener frame 52 for comfort and to prevent chafing of the wearer.

When the end of strap 20a forming the tongue 54 and the fastener frame 50 at the opposite end of the strap 20a are pulled towards each other, force is exerted simultaneously along the bottom strap portion 32 and along the top strap portion 30, resulting in a distribution of support across substantially the full vertical plane of the device 10a at the lumbar region. Support across the width of the back resists the tendency of the device to conform to the vertical curvature of the body, and thereby prevents the attached lumbar support pad 16a from moving away from the back and thereby reducing its effectiveness.

In both the single and dual strap embodiments 10a, 10b, the lumbar support pad 16 extends substantially from the top of the body 14 to the bottom of the body 14 and from the top of the belt 12 to the bottom of the belt 12, thereby providing support at the lumbar of the wearer across the width of the device (that is, the height of the pad 16 along its vertical axis).

The bodies 14 and belt straps 20 can be made from a wide variety of materials, including natural or organic materials such as leather, without affecting their functionality. Each belt strap 20 is preferably made from a single piece of flat synthetic fiber web, and the body 14 is preferably of unitary, one-piece, integral construction made of an elongate flat piece of synthetic fiber web. The lumbar support pad 16 is preferably made from a single piece of synthetic fiber web pack cloth forming an envelope and a contoured resilient synthetic rubber padding disposed in the envelope. The term "synthetic fiber web" refers to the family or families of man-made materials selected for their strength, flexibility, light weight, durability, cost, availability, and consistency —— e.g., nylon and related man-made fibrous materials.

The padding substance is central to the construction of the contoured lumbar support pad 16. A solid elastic substance with the properties of firmness in texture and resilience is required. Synthetic rubber is preferably used because these properties can be acquired precisely and consistently. A preferred synthetic rubber material is available under the tradename Rubatex.

The useful fasteners 18 for securing the device 10 to the wearer are varied. A fastener system that permits precise incremental or continuous adjustments is required for maximum effectiveness, although fastener systems permitting only discrete or fixedly spaced adjustments may be used. A slide-lock buckle, a tape fastener system (e.g., a hook and loop type tape fastener of the type available under the trade name Velcro), a combination of both, or similar incrementally adjustable fasteners are preferred. The devices are described herein as using a tape fastener system.

The terms "contoured" and "articulated," as used herein to describe the lumbar support pad 16 indicate, respectively, that the face thereof adjacent the wearer is not planar or flat, and that the various outer sections 44a thereof are movable (i.e., articulated) relative to the central section 44b thereof, thereby allowing the pad face adjacent the wearer's back to conform thereto.

The present invention also encompasses a more economical, but possibly less comfortable, embodiment of the orthopedic device wherein there is no flexible flat body and the flexible belt 12 is operatively secured (e.g., by stitching) to the lumbar support pad 16 adjacent a pair of opposed ends thereof in the horizontal plane.

To summarize, the present invention provides an orthopedic device affording balanced, equal, and uninterrupted support to the lumbar region along the entire horizontal and vertical planes thereof. The device is of simple and rugged construction, economical to manufacture, use and maintain.

Now that the preferred embodiments of the present invention have been shown and described in detail, various modifications and improvements thereon will become readily apparent to those skilled in the art. Accordingly, the spirit and scope of the present invention is to be construed broadly and limited only by the appended claims, and not by the foregoing disclosure.

We claim:

1. An orthopedic device to provide lower back support for a wearer during active movement of the wearer, comprising:
   (A) a flexible flat body;
   (B) a resilient contoured lumbar support pad of varying thickness secured to said body; said pad comprising a plurality of articulated sections including a center section of at least a first thickness adapted to be positioned over the spine of the wearer and wide enough to fill the gap at the spine between the erector muscles of the wearer, and at least one side section of a second thickness disposed on each side of said center section and adapted to be positioned adjacent the erector muscles of the wearer, said first thickness being substantially greater than said second thickness in order to apply pressure directly to the spine rather than only indirectly through the erector muscles; and
   (C) a flexible belt traversing said pad and secured to said body at points beyond said pad, said belt being configured and dimensioned to extend substantially completely about the waist of the wearer and be secured thereabout for positioning said pad on the lumbar region of the wearer to fill the concave area formed by the spine and the erector muscles.

2. The device of claim 1 wherein said body is of one-piece, integral, unitary construction.

3. The device of claim 2 wherein said center section has a thickness along its central vertical axis which is greater than its thickness to either side.

4. The device of claim 1 wherein said body has a pair of opposed faces, and said pad is secured to the face adjacent the wearer, when worn, and said belt is secured to the opposite face.

5. The device of claim 1 wherein said pad extends substantially from the top of said body to the bottom of said body, thereby to provide support at the lumbar of the wearer across the vertical height of the device.

6. The device of claim 1 wherein said pad extends substantially from the top of said belt to the bottom of said belt, thereby to provide support at the lumbar of the wearer across the vertical height of the device.

7. The device of claim 1 wherein said belt consists essentially of two vertically spaced straps secured to said body in parallel disposition and releasable fastener means secured to each strap for securing together the ends of each strap independently about the wearer's waist.

8. The device of claim 7 wherein said pair of straps trisect the vertical height of said body.

9. The device of claim 1 wherein said belt consists essentially of a single strap and releasable fastener means secured thereto for securing the belt about the wearer's waist.

10. The device of claim 1 wherein said device consists essentially of said body, said pad, and said belt.

11. An orthopedic device to provide lower back support for a wearer during active movement of the wearer, comprising:
(A) a flexible flat body;
(B) a resilient contoured lumbar support pad of varying thickness secured to said body; said pad comprising a plurality of articulated sections including a center section of at least a first thickness adapted to be positioned over the spine of the wearer and wide enough to fill the gap at the spine between the erector muscles of the wearer, and at least one side section of a second thickness disposed on each side of said center section and adapted to be positioned adjacent the erector muscles of the wearer, said first thickness being substantially greater than said second thickness in order to apply pressure directly to the spine rather than only indirectly through the erector muscles; and
(C) a flexible belt traversing said pad and secured to said body at points beyond said pad, said belt being configured and dimensioned to be secured about the waist of the wearer to fill the concave area formed by the spine and the erector muscles; said belt consisting essentially of a single strap and releasable fastener means secured thereto for securing the belt about the wearer's waist, said strap being secured to said body in a generally elliptical configuration with the long axis thereof generally horizontal, said strap having one end secured to a first point at the center of one end of said body, extending in an upward arc, with the apex of said upward arc near the upper edge of the middle of said body, and descending to a second point at the center of the opposite end of said body, where said strap forms a loop extending beyond said opposite body end and is secured to said second point, said strap also extending from said second point in a downward arc, with the nadir of said downward arc near the lower edge of the middle of said body opposite said apex, and rising to cross-join and overlap said strap one end at said first point, thereby to complete the generally elliptical configuration, and finally extending beyond said one body end to form a tongue for fastening.

12. The device of claim 11 wherein said fastener means includes a tape fastener system affixed to the outside face of said tongue.

13. The device of claim 12 wherein said fastener means includes a fastener frame defining a slot for receiving the free end of said tongue, and said loop of said strap extends through said slot.

14. An orthopedic device to provide lower back support for a wearer during active movement of the wearer, comprising:
(A) a flexible flat body of one-piece, integral unitary construction having a pair of opposed faces;
(B) a resilient contoured lumbar support pad of varying thickness secured to said body; said pad defining a plurality of articulated sections, including a center section of at least a first thickness adapted to be positioned over the spine of the wearer and wide enough to fill the concave gap at the spine between the erector muscles of the wearer, and at least one side section of a second thickness disposed on each side of said center section and adapted to be positioned adjacent the erector muscles of the wearer, said first thickness being substantially greater than said second thickness and said center section having a thickness along its central vertical axis which is greater than its thickness to either side; and
(C) a flexible belt traversing said pad and secured to said body at points beyond said pad, said belt being configured and dimensioned to extend substantially completely about the waist of the wearer and be secured thereabout for positioning said pad on the lumbar region of the wearer;
said pad being secured to the face of said body adjacent the wearer, when worn, and said belt being secured to the opposite face of said body, said pad extending substantially from the top of said belt to the bottom of said belt, thereby to provide support at the lumbar of the wearer across the vertical height of the device.

15. The device of claim 14 wherein said belt consists essentially of two vertically spaced straps secured to said body in parallel disposition and releasable fastener means secured to each strap for securing together the ends of each strap independently about the wearer's waist, said pair of straps trisecting the height of said body.

16. The device of claim 14 wherein said device consists essentially of said body, said pad, and said belt.

17. An orthopedic device to provide lower back support for a wearer during active movement of the wearer, comprising;
(A) a flexible flat body of one-piece, integral unitary construction having a pair of opposed faces;
(B) a resilient contoured lumbar support pad of varying thickness secured to said body; said pad defining a plurality of articulated sections, including a center section of at least a first thickness adapted to be positioned over the spine of the wearer and wide enough to fill the concave gap at the spine between the erector muscles of the wearer, and at least one side section of a second thickness disposed on each side of said center section and adapted to be positioned adjacent the erector muscles of the wearer, said first thickness being substantially greater than said second thickness and said center section having a thickness along its central vertical axis which is greater than its thickness to either side; and (C) a flexible belt traversing said pad and secured to said body at points beyond said pad, said belt being configured and dimensioned to be secured about the waist of the wearer for positioning said pad on the lumbar region of the wearer;

said pad being secured to the face of said body adjacent the wearer, when worn, and said belt being secured to the opposite face of said body, said pad extending substantially from the top of said belt to the bottom of said belt, thereby to provide support at the lumbar of the wearer across the vertical height of the device;

said belt consisting essentially of a single strap and releasable fastener means secured thereto for securing the belt about the wearer's waist, said strap being secured to said body in a generally elliptical configuration with the long axis thereof generally horizontal, said strap having one end secured to a first point at the center of one end of said body, extending in an upward arc, with the apex of said upward arc near the upper edge of the middle of said body, and descending to a second point at the center of the opposite end of said body, where said strap forms a loop extending beyond said opposite body end and is secured to said second point, said strap also extending from said second point in a downward arc, with the nadir of said downward arc near the lower edge of the middle of said body opposite said apex, and rising to cross-join and overlap said strap one end at said first point, thereby to complete the generally elliptical configuration, and finally extending beyond said one body end to form a tongue for fastening.

* * * * *